United States Patent [19]

Masopust

[11] Patent Number: 5,339,827
[45] Date of Patent: Aug. 23, 1994

[54] ACUPUNCTURE SYSTEM AND METHOD

[75] Inventor: Jiri Masopust, Rodinna, Czechoslovakia

[73] Assignee: Intech Scientific, Inc., Closter, N.J.

[21] Appl. No.: 16,745

[22] Filed: Feb. 11, 1993

[51] Int. Cl.$^5$ .......................................... A61H 39/02
[52] U.S. Cl. .................... 128/735; 128/907
[58] Field of Search ........... 128/734, 735, 907, 419 R, 128/420 R, 421, 422, 423 R

[56] References Cited

U.S. PATENT DOCUMENTS

| | | | |
|---|---|---|---|
| 4,016,870 | 4/1977 | Lock | 128/735 |
| 4,408,617 | 10/1983 | Auguste | 128/735 |
| 5,012,816 | 5/1991 | Lederer | 128/735 |

FOREIGN PATENT DOCUMENTS

| | | | |
|---|---|---|---|
| 2944169 | 5/1981 | Fed. Rep. of Germany | 128/735 |
| 1101230 | 7/1984 | U.S.S.R. | 128/735 |

Primary Examiner—Max Hindenburg
Attorney, Agent, or Firm—Eliot S. Gerber

[57] ABSTRACT

A method and system to find and analyze acupuncture points in which a probe uses alternating current with a high content of harmonic components. The current's frequency is set to be inversely proportional to the impedance at the point and preferably is about 1 kHz at 10000 ohm impedance level. The amplitude of measuring current is also inversely proportional to the impedance at the measured point. The output frequency is identical with the measuring frequency and is inversely proportional to the point's impedance. The hardware includes a reference electrode, such as a hand-held "grabber" metal stick and a measuring electrode (probe). The surface of the reference electrode is preferably about a hundred times larger than that of the measuring electrode. Both electrodes are connected to an impedance-to-frequency converter. The impedance-to-frequency converter is connected to the input port of a PC (Personal Computer) having a screen to display the impedance at each acupuncture point. The computer stores the impedance measured at each acupuncture point in memory when a switch on the probe is activated, and analyzes the stored data, for example, by comparing the impedances at various selected acupuncture points.

8 Claims, 4 Drawing Sheets

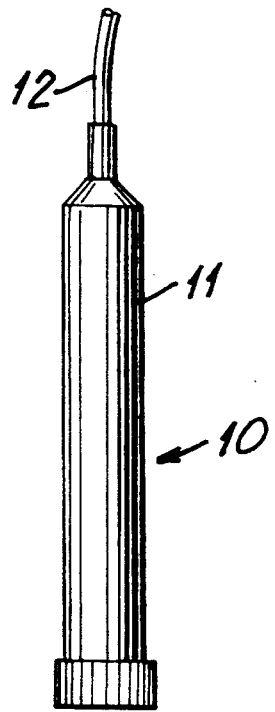
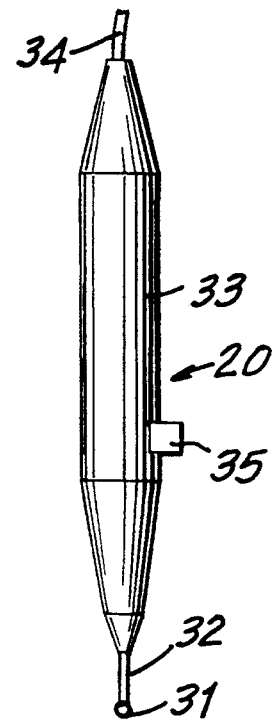
FIG.4  FIG.5
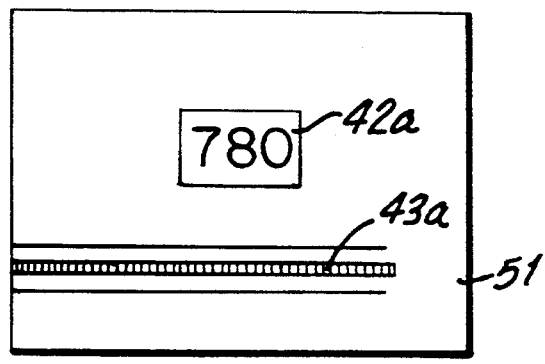
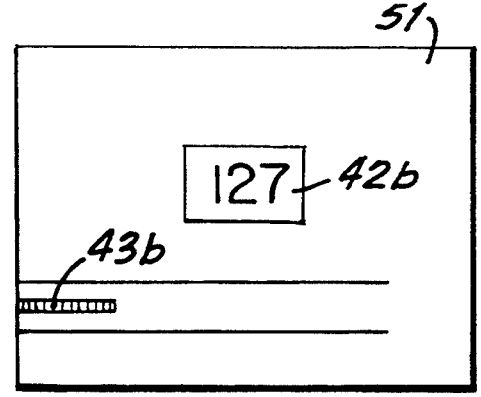
FIG.6A  FIG.6B

ACUPUNCTURE SYSTEM AND METHOD

FIELD OF THE INVENTION

The present invention relates to medical systems and methods for acupuncture and more particularly to such systems and methods for finding the active acupuncture points (sites) on the human body, measuring the electrical impedance at the points, and analyzing of the electrical activity at such points.

BACKGROUND OF THE INVENTION

Acupuncture is one of the oldest forms of medical practice and has been used in China for thousands of years. The general theory is that the body has energy in the form of "Qi" (chee) and "blood" which extends through the body organs and appears, in lines and points, on the skin. Each active point (site) on the skin is called an "acupuncture point" ("men" or "gates") and is very small, in the order of one square millimeter.

After the proper acupuncture points are located, the patient may be treated using those points. The traditional Chinese treatment is to inject needles (thin, solid, stainless-steel needles), at various depths, through the acupuncture points. More recently, various practitioners have also used laser beam (light), pressure (massage) and electrical stimulation applied to the selected acupuncture points.

A skilled acupuncturist, who may have been trained for years, is able to find the acupuncture points by feeling with his/her fingers. The acupuncture points, in various versions, have been published in charts and in written descriptions. However, due to individual differences, such as differences in the size and shape of patients, even experienced acupuncture practitioners who rely on "body units" (width of the second joint of the thumb), may have difficulty correctly locating the acupuncture points. In addition, the location of those points may be time-consuming and acupuncturists, to avoid embarrassment and delay, may use points which are close to the accepted acupuncture points, but are not exactly at those points.

The interest in methods used by eastern medicine, especially acupuncture, is growing rapidly in the west. Some patients believe that methods employed by eastern medicine are simpler and may in some cases lead to better results, compared to traditional western methods of diagnostics and healing. Successful eastern healers often have enormous experience and knowledge and acquired their skills in strict training and years of practicing.

In recent years, it has been shown, in the patent literature and elsewhere, that traditional eastern methods can be modified using electronic devices to reach results faster without the loss of effectiveness. Modern electronics can make eastern acupuncture methods more accessible to the western medical community.

The basis for eastern methods is acupuncture diagnosis which in turn stems from correct determination of the activity in individual acupuncture points. Without such diagnosis the treatment is aimless and less effective, regardless which treatment method is selected.

The traditional Chinese medicine identifies a large number of acupuncture points on the human body which differ slightly in their physical properties. FIG. 1 shows an example of acupuncture points on the left hand, the points being shown as small circles. By electronically measuring certain physical properties, one can obtain the same information as might be obtained by a highly skilled master of classical acupuncture, using classical methods. Hence, electronic measurement of acupuncture point activity can provide reproducible information with less extensive operator training in acupuncture.

By examining the electrical properties in acupuncture points, it is possible to determine the electrical point-to-point properties of electrical potential (voltage), resistance and impedance. However, measuring of electrical potential (voltage) requires a relatively complex apparatus, as common electromagnetic noise can cause significant errors. Measuring the d.c. resistance is influenced by the following: tissue polarization, electrochemical potential found at the contact point of the electrode with the skin and the electro-conductivity of the skin. Because of these disturbing factors, the measured potential and resistance values are difficult to reproduce and measurement methods, based on d.c. resistance, must include complex procedures to compensate for the disturbing factors.

The measuring of impedance using alternating current (a.c.) is more precise. The acupuncture point is defined as a point on the skin with smallest impedance value relative to the immediate surroundings. Using a.c. impedance measurement, there is no tissue polarization and the electrochemical potentials because at the contact point they compensate each other. Moreover, since the impedance capacity component dominates ($Z=R-j'Xc$), the influence of resistance in the contact point is diminished and the measurements are more accurate. The problem remains to select the proper frequency of the measuring current and the measuring current's amplitude.

U.S. Pat. No. 4,016,870 ("Lock '870 patent"), entitled "Electronic Acupuncture Point Finder" states that the acupuncture points coincide with points of low body impedance. It discusses prior devices using an oscillator in which a tone changes as the finder probe passes over an acupuncture point. The Lock '870 patent discloses a battery operated "on-off" point finder probe and a hand-held "grabber" electrode. The impedance difference of points touched by the finder probe are compared with a set of fixed impedances (impedance bridge) to distinguish abnormal impedance points, by an imbalance signal. The points are indicated by an on-off ammeter, a pulse tone, and two lights. The impedance difference is used to find acupuncture points; but the points are not measured in ohms or analyzed.

U.S. Pat. No. 4,408,617 is entitled "Apparatus For Detecting The Acupuncture Points On A Patient And For Applying Electrical Stimulating Signals To the Detected Points" ("August '617 patent"). A generator (oscillator) delivers a sawtooth signal to the needle of a probe. The impedance difference is used to find acupuncture points; but the points are not measured in ohms or analyzed.

OBJECTIVES OF THE INVENTION

It is an objective of the present invention to provide a measuring system and method to find acupuncture points based on the measuring of impedance of such points, the display of the measurements on a screen while the measurements are being made, and recording and analyzing the measured impedances of the points.

It is another objective of the present invention to make the measurement less dependent on the skill of the operator and to make it accurate and reproducible.

It is another objective of the present invention to limit the influence on the acupuncture point during actual measurement by selecting and controlling both the optimal frequency and measuring current of the probe.

It is another objective of the present invention to provide output data to a data acquisition system, such as a PC, to allow speedy data collection from acupuncture points and their evaluation, charting, trend analysis, and data base storage.

It is another objective of the present invention to accurately control the needed stimulation current based on the impedance at the acupuncture point and a calculated value determined by computer software.

It is another objective of the present invention to simplify the entire process of acupuncture based diagnosis and to shorten the time needed to train medical technicians and users in the use this branch of eastern medicine.

SUMMARY OF THE INVENTION

The present invention relates to a system and method for measuring the electrical activity of acupuncture points in order to find such points and using computer software to perform an analysis on the measured activity by a comparison of the measured impedance at a plurality of selected acupuncture points.

The method is based on the underlying principle of sending alternating current through the acupuncture point, the current having a high content of harmonic components. The current frequency is set automatically, by the circuitry, to be inversely proportional to the impedance in the point and is preferably about 1 kHz at 10K ohms impedance level. The current amplitude is also inversely proportional to the impedance at the acupuncture point. If the impedance is high, then both the measuring frequency and amplitude at the measuring probe decline. This method allows the reading of energy level (activity) in the acupuncture point with a minimum of error due to outside influences. For example, for low level of activity (high impedance at the point) when the influence of outside disturbance factors is highest, both the frequency and the level of measuring current are low. In the case of high activity level (lower impedances at the point) the frequency and measuring current are higher and the accuracy of the measurement increases.

The test equipment consists of the two electrodes, one for reference and one for point measurement. The point measuring electrode is a probe having a metal end with a smaller surface than the surface of the acupuncture point (about 1 mm square). The reference electrode surface is at least 25 times larger and preferably 100 times larger and is preferably a "grabber" electrode—a metal stick held in the patient's hand. The adequately sized surface of this reference electrode largely eliminates the influence of the placement of the electrode during measuring and it can be placed anywhere on the body. The two electrodes are connected to the entry ports of an impedance-to-frequency converter. The measuring frequency of this converter is inversely proportional to the impedance of the acupuncture point relative to the reference electrode. The measuring frequency is set by an astable multivibrator, the frequency of which is set by internal values of the MV and the impedance at the frequency point. The converter's output signal is a signal whose frequency is the same as the measuring frequency and is inversely proportional to the impedance being measured, i.e., when the impedance is low the output frequency is also high.

Before measuring, the circuitry produces only a direct voltage output. When the probe electrode touches the body, at the acupuncture point, current starts flowing through the circuit, consisting of the reference electrode, body, the probe electrode and the converter. Depending on the intensity of the flowing current after a certain time, when the capacitor is "filled up", the direction of the current flow reverses. When the capacitor is being discharged at the same rate, i.e., the time to discharge is the same as the time to charge. When the capacitor is discharged, the current flow direction is again reversed. The frequency is set automatically by the time for one cycle of charge-discharge. When the impedance is high, the current is low and the time needed to charge/discharge the capacitor is long, hence low frequency, i.e., the frequency is inversely proportional to the impedance level.

Some of the advantages of the method, hardware and software of the present invention are that the impedance at the acupuncture point can be determined by measuring the period, or output frequency, at the converter. The analysis and evaluation of the output frequency is preferably made by the connected PC (Personal Computer). This allows automatization of measurements, data evaluation, and data base storage. It also represents a link between eastern and western diagnostic methods by converting information about the human body previously determined by highly skilled acupuncturists, to objectively obtainable data points, which are reproducible. The link between the two cultures hinges on the reproducibiity of measured data, relied upon by western medicine.

BRIEF DESCRIPTION OF THE DRAWINGS

Other objectives of the present invention will be apparent from the following detailed description, taken in conjunction with the accompanying drawings.

In the drawings:

FIG. 4 is a front plan view of a reference electrode;

FIG. 5 is a front plan view of a probe measuring electrode;

FIGS. 6A and 6B are displays on the computer monitor screen showing impedance measurements.

DESCRIPTION OF THE PREFERRED EMBODIMENT

Figure 1:
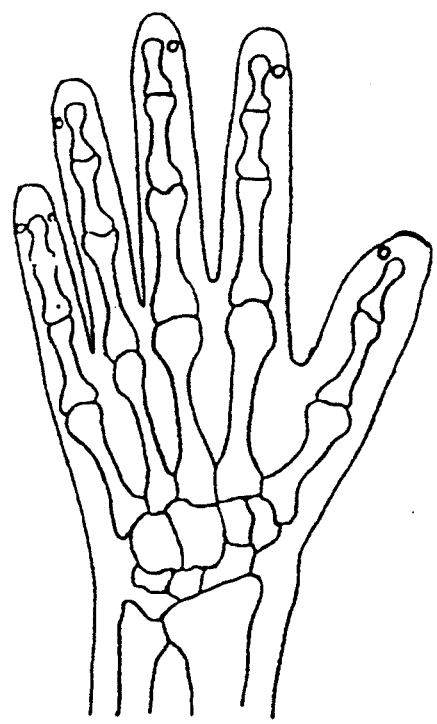
FIG. 1 is a top plan view of a human hand illustrating some acupuncture points on the skin of the hand.

The measurement method is based on the use of a measuring signal having a high content of harmonic components. The frequency and amplitude of the signal changes relative to the measured impedance which reflects the activity at the acupuncture point and is inversely proportional to the measured impedance. Preferably at a measured impedance of 10000 ohms (10K ohms) the frequency is 1 kHz and the current is about 100 microamperes (0.1 milliamperes). The galvanic effect is compensated by utilizing symmetrical alternating current.

The measuring hardware consists of the reference electrode 10 and a probe electrode 20, both connected to the impedance/frequency converter 30, and a digital computer 50, preferably a PC (Personal Computer) having a screen 51.

In the drawing FIG. 5 the end contact surface 31 (point) of the probe measuring electrode 20 has a spheroid shape and has a skin contact surface about one square millimeter. The probe electrode 20 has a spring-loaded metal rod 32 having spheroid-shaped contact end surface 31 which is less than about 5 mm square and preferably is about 1 mm square. Probe electrode 20 has a plastic (non-conductive) body 33, to be held by the user's hand and a multi-conductor shielded cable 34. The rod 32 is normally extended by the spring (not shown) and is connected to one of the wires of the cable 34. The push switch 35 (on-off, normally off) is connected other wires of the cable 34. In an examination, typically the probe electrode 20 is held and operated by the examiner, for a example, a doctor or nurse. However, when the patient performs a self-examination, for example, to daily monitor the effect of a medicine, the patient holds and operates the probe electrode 20. In that case, the reference electrode 10 may be, for example, a metal plate held to the patient's arm or leg by a band, in order to free both of the patient's hands.

As shown in FIG. 4, the reference electrode 10 ("grabber electrode") has a metal surface 11 with a cylindrical shape having a surface at least 25 times larger and preferably about a hundred times larger than the probe point 31; i.e., at least 100 square millimeters. Preferably the reference electrode 10 fits in one hand of the patient. The metal surface 11 of the reference electrode 10 is electrically connected to the converter 30 by shielded cable 12 (single conductor).

Figure 2:
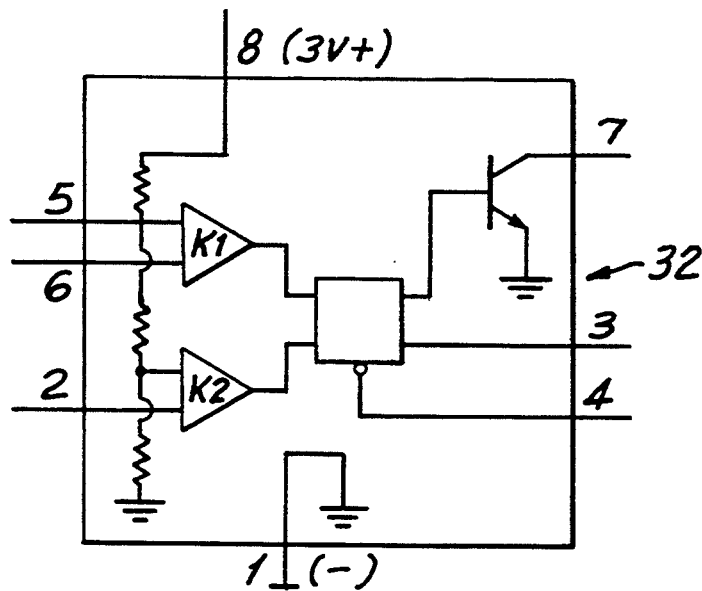
FIG. 2 is an internal block diagram of a suitable integrated circuit used in the system of the present invention.
Figure 3:
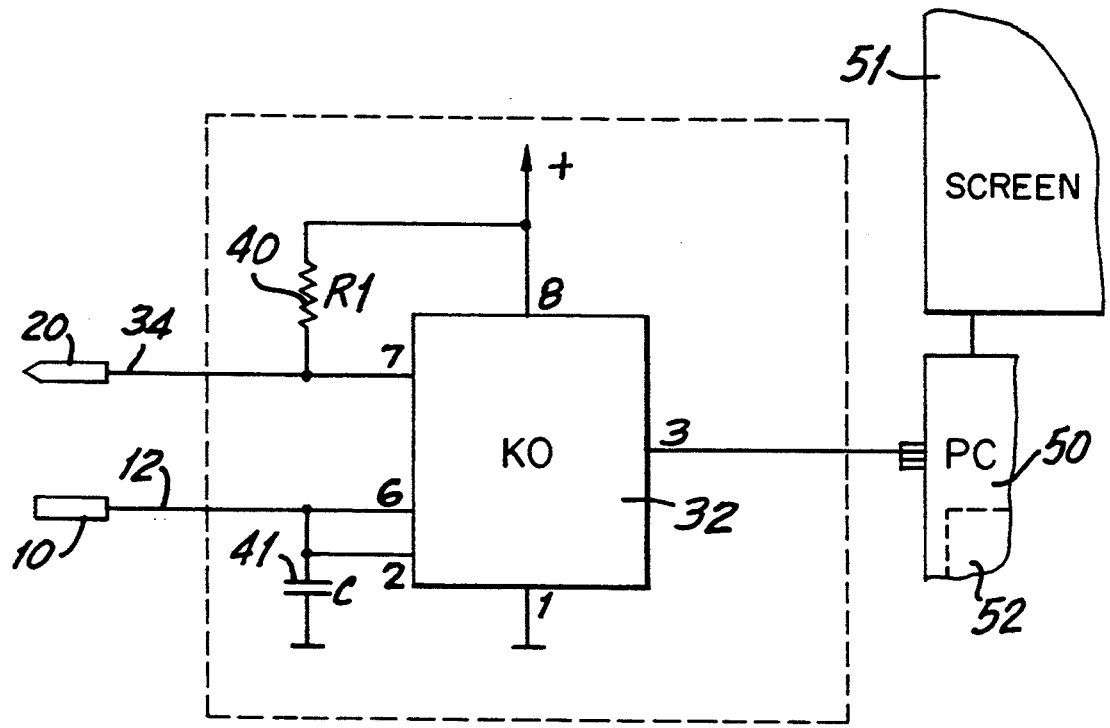
FIG. 3 is a block diagram of the system of the present invention.

The measuring current and frequency of the converter 30 are inversely proportional to the impedance of the acupuncture point and its output frequency is identical to that of the measuring frequency. The higher the measured impedance, the lower the input current and frequency. The impedance frequency converter 30 preferably includes an integrated NE 555 circuit 32 (Ko) and is shown in FIG. 3. The internal connections of this circuit 32 (Ko) are shown in FIG. 2. As shown in FIG. 3, this integrated circuit 32 has negative supply voltage on pin 1 and positive supply voltage of 3 V on pin 8. Resistor R1 (40) with resistance of 390 ohms is connected between pin 7 and pin 8. The comparator pins 2 and 6 are connected to one side of the condenser 41 (C) with 68 nF capacity. The other side of the condenser 41 (C) is connected to the negative supply voltage pin 1.

FIG. 2 shows the schematics and internal connection of integrated circuit 32 (IC NE 555) which operates as a sawtooth wave generator and an astable multivibrator.

Description of pin assignments:
1—Ground (negative)
2—Low comparator
3—Output
4—Reset
5—Divider
6—High comparator
7—Discharge
8—VCC (3 volts +)

In operation, the reference electrode 10 is placed anywhere on the body surface, i.e., it can be held in one hand, and the probe electrode 20 is used to find the acupuncture point. When the point of probe electrode 20 touches the acupuncture point, the circuit between electrodes 10 and 20 is closed. At that time condenser 41 is alternatively charged through resistor R1 and the measured impedance at the acupuncture point. The condenser 41 is discharged through the measured impedance by pin 7 of integrated circuit 32. The impedance between the two electrodes 10 and 20 and condenser 41 determines a time constant of the astable multivibrator, represented by the integral circuit 32, condenser 41, resistor 40 and measured impedance, and its frequency. Condenser 41 (C) is then alternately charged to 2/3 VCC (threshold of comparator K1, FIG. 2) and discharged to 1/3 VCC threshold of comparator K2, FIG. 2) of the supply voltage with the same frequency. These thresholds are fixed so that the amplitude of the measuring voltage remains constant. This establishes that the measuring current is inversely proportional to the impedance, i.e., the higher the impedance the lower the amplitude of the measuring current. The direction of the measuring current depends on whether the condenser 41 (C) is charged or discharged. The current direction reverses with each change from charge to discharge and vice versa, and this direction reversal guarantees that both voltage and current are alternating. Because the measured impedance is much higher than the resistance of resistor 40 (R1) the keying interval is practically 1.1, i.e., the resistor presents no influence on the time difference if charged and discharged. With the activating discharge rhythm on pin 7 (a discharge port), there are pulses found on the output pin 3. The frequency of these output pulses on pin 3 is inversely proportional to the measured impedance (activity) at the acupuncture point. The output on pin 3 is electrically connected at an input port of computer 50.

The computer 50 (PC) has a screen 51 which displays the impedances as they are being measured and displays the results of the analysis performed in the computer 50 under software control. The software program is loaded into the digital memory of the computer 50, for example, by means of a floppy disk, before the measurements are started.

As shown in FIG. 6A, the screen 51 shows the impedance (in ohms or proportional to ohms) as a digital number 42a, which is relatively high. In addition, a horizontal moving bar 43a varies in its length in accord with the impedance measured by the probe. The examiner finds the acupuncture points, which are points of relatively low impedance, by watching the numbers 42 and moving bar 43 and seeks and moves the probe until the number 42 is reduced and the bar 43 is shortened. He then operates button 35 to record the impedance. The measured impedance is recorded and stored in digital memory 52 in the computer 50.

As shown in FIG. 6B, the probe has found an acupuncture point because the number 42b is relatively low and the bar 43b is relatively short. Consequently, the examiner (user) will operate button 35. The program, shown on screen 51, directs the examiner to each acupuncture point in turn (one after the other) so that a recorded impedance is associated with each acupuncture point, by operation of button 35, to form a list of points and their measured impedances (in ohms).

Figure 7:
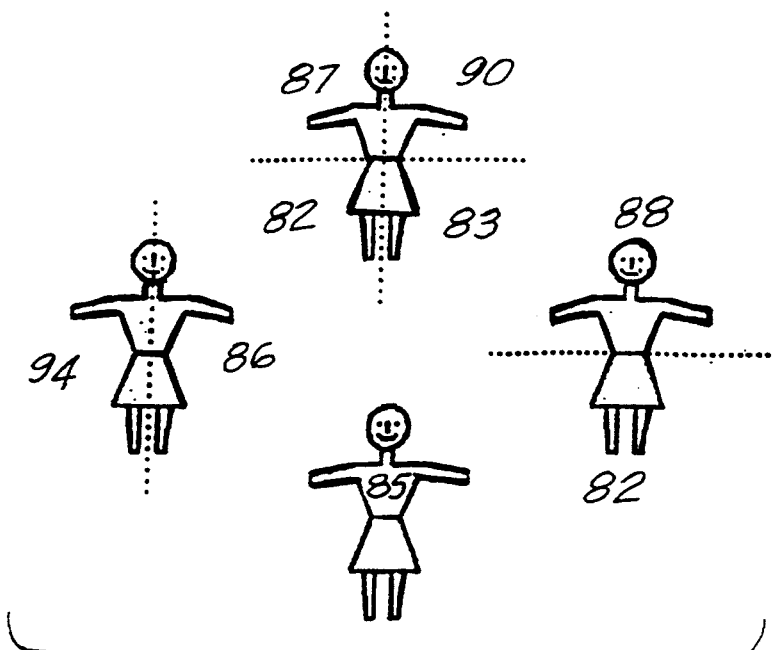
FIGS. 7 and 8 are displays on the computer monitor screen showing results of acupuncture analyses.

FIG. 7 illustrates the results of the analysis of the impedances stored in computer memory 52. The software preferably analyzes the measured impedances in four quadrants of the body (RU—right upper; LU—left upper; RL—right lower; LL—left lower). If one quadrant is out of balance (impedances relatively high or low) there may be a medical problem indicated as being associated with that quadrant or indicated by the acupuncture points of that quadrant. This is only one example of the many possible analysis systems that may be used with the recorded list of acupuncture points and their associated impedances. Also, FIG. 7 shows an analysis by halves (upper, lower, right, left), the left and right halves being illustrated. Also the calculated average, over all acupuncture points, is illustrated.

Figure 8:
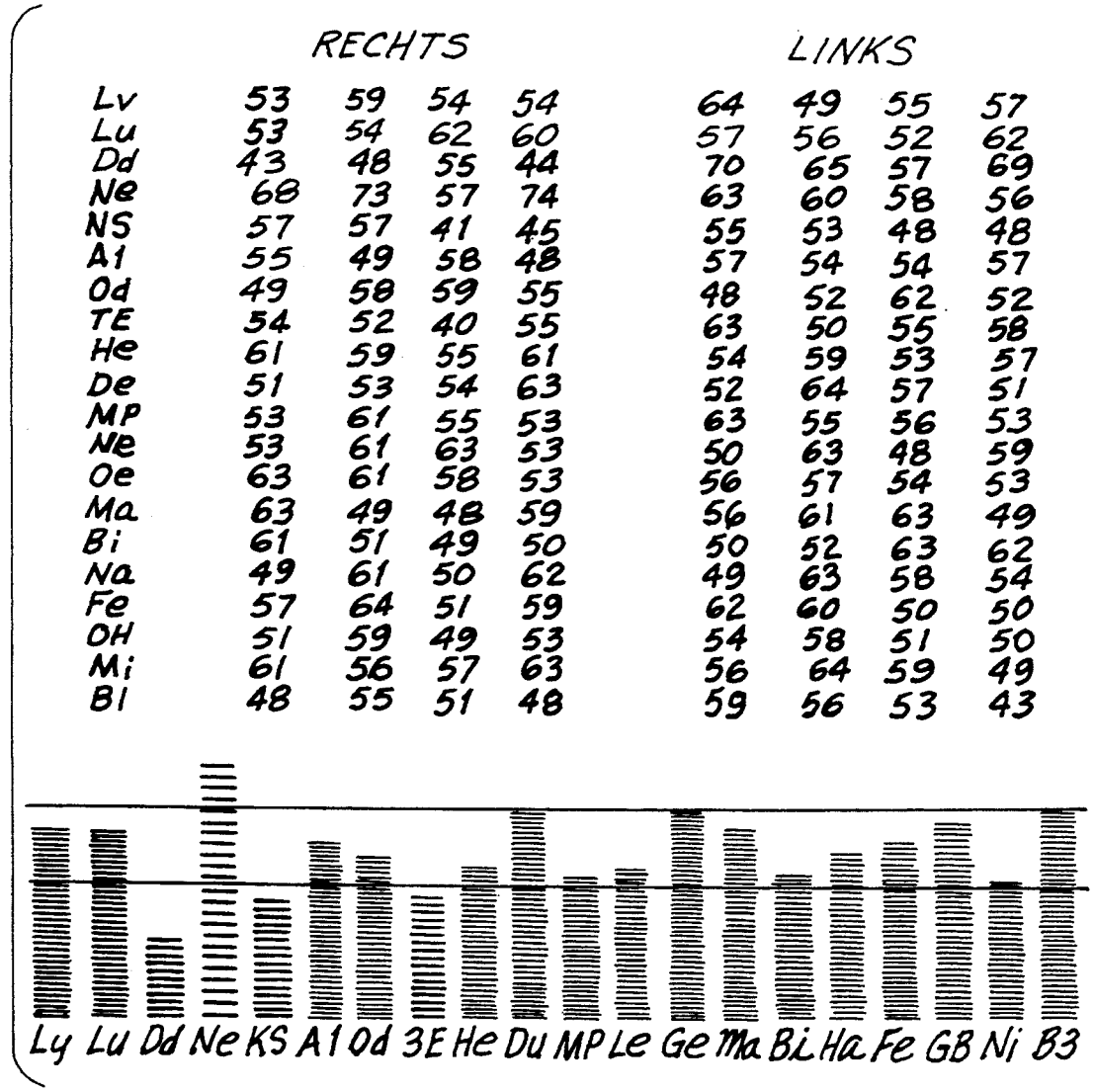

FIG. 8 shows a typical impedance set of numbers for the eight acupuncture points 4 right ("RECHTS") and 4 left ("LINKS") associated with each organ. At the bottom a graph chart shows the results of the software analysis for each body organ. For example, "Lung" (i.e., lung) is in the normal range between lines 70 and 71.

I claim:

1. A system for helping find acupuncture points on a human patient and the recording, storage and analysis of the electrical impedance of the points after they are found, including
   (i) a probe electrode having a conductive end, the size of the end being less than about 1 mm square;
   (ii) a reference electrode having a conductive surface area at least 25 times larger than the probe conductive end;
   (iii) oscillator means to generate an oscillatory waveform with a high content of harmonic components, the oscillator means being electrically connected to the probe conductive end;
   (iv) an impedance-to-frequency converter means connected to the probe electrode and reference electrode to convert the impedance measured at the probe conductive end to an electrical frequency;
   (v) a computer system means electrically connected to the impedance-to-frequency converter means to display the impedances as they are being measured by the probe electrode on a screen; the computer system means having a display screen, digital memory and programmed software means to analyze the impedances at the found acupuncture points.

2. A system as in claim 1 and including frequency setting means to control the frequency of the oscillatory waveform to be inversely proportional to the impedance being measured.

3. A system as in claim 1 wherein the oscillatory waveform has a frequency of about 1 kHz at an impedance of 10000 ohms.

4. A system as in claim 1 and including amplitude setting means to set the amplitude of the measuring current to be inversely proportional to the impedance being measured.

5. A method to help find acupuncture points on a human patient and the recording, storage and analysis of the electrical impedance of the points after they are found, including the steps of:
   (i) measuring skin areas of the patient using a probe electrode having a conductive end whose end size is about 1 mm square over the skin of the patient;
   (ii) simultaneously touching the skin of the patient with a reference electrode having a conductive surface area at least 100 times larger than the conductive probe end;
   (iii) generating an oscillatory waveform having a high content of harmonic components and conducting the oscillatory waveform to the probe electrode end;
   (iv) converting an electrical signal form the probe conductive end to an output frequency using an impedance-to-frequency converter connected to the probe point electrode and reference electrode;
   (v) displaying the impedances measured by the probe conductive end on a screen while they are being measured using a computer system electrically connected to the impedance-to-frequency converter, the computer system having a display screen, digital memory and programmed software means to analyze the impedances at the found acupuncture points.

6. A method as in claim 5 and further including controlling the frequency of the oscillatory waveform to be inversely proportional to the impedance being measured.

7. A method as in claim 5 wherein the oscillatory waveform has a frequency of about 1 kHz at an impedance of 10000 ohms.

8. A method as in claim 5 and further including setting the amplitude of the measuring current to be inversely proportional to the impedance being measured.

* * * * *